United States Patent [19]

Maaskamp

[11] Patent Number: 4,722,366
[45] Date of Patent: Feb. 2, 1988

[54] FLOW CONTROL DEVICE

[76] Inventor: Armand Maaskamp, 27675 Alarcon, Mission Viego, Calif. 92691

[21] Appl. No.: 19,357

[22] Filed: Feb. 26, 1987

[51] Int. Cl.$^4$ ............................................. F16K 11/06
[52] U.S. Cl. .................................... 137/893; 137/550;
            137/876; 251/345; 285/325; 604/119; 604/319
[58] Field of Search ............... 137/544, 550, 888, 892,
            137/893, 872, 876; 251/341, 343, 344, 345;
                                    285/156, 325; 604/119, 319

[56] References Cited

U.S. PATENT DOCUMENTS

| | | | |
|---|---|---|---|
| 3,998,227 | 12/1976 | Holbrook et al. | 604/319 X |
| 4,180,074 | 12/1979 | Murray et al. | 604/119 X |
| 4,253,684 | 3/1981 | Tolbert et al. | 285/156 X |
| 4,560,144 | 12/1985 | Williams et al. | 604/119 X |

*Primary Examiner*—A. Michael Chambers
*Assistant Examiner*—John C. Fox
*Attorney, Agent, or Firm*—Bogucki, Scherlacher, Mok & Roth

[57] ABSTRACT

A male fluid control member for controlling aspiration flow is insertable in a standard female receptacle having an interior cylindrical recess including a vent line leading to the recess. The male member includes an open end intruding into the recess in the female receptacle and filled by a protruding resilient gasket having a central orifice. The end recess is in communication with an interior chamber that extends along the aspiration fluid flow path, but is sealed therefrom by a hydrophobic membrane of substantial cross-sectional area. In operating position the orifice in the gasket in the male member is aligned with the vent line and the gasket and membrane seal the conduit thus formed from external sources of contamination. The opening in the gasket diverges in the direction toward the membrane which, together with the interior chamber, has a substantial cross-section. Thus fluid in the aspiration line flows freely through the male member without egressing toward the vent line, while venting air introduced into the aspiration line is sterile. There is thus no danger of cross-contamination due to prior use or external sources, and the device provides fluid control in the usual manner.

12 Claims, 10 Drawing Figures

FLOW CONTROL DEVICE

BACKGROUND OF THE INVENTION

Ophthalmic surgeons and supporting personnel widely employ particular known systems for irrigation of the eye and the extraction of matter during eye surgery. In one widely used system, the eye is constantly irrigated with a sterile solution during the operation, and the irrigating fluid, as well as particle matter, fragments and the like are drawn off along an aspiration line via a suction tip. This system is particularly used in both phacoemulsification and extra capsular cataract extraction (ECCE) procedures for the exraction of the lens of an eye in which a cataract has developed.

A flow control device which vents to atmosphere is also employed in communication with this aspiration line. The control device is operated by the surgeon, so that aspiration can be modulated in accordance with his immediate needs during surgery. Need may also arise to terminate aspiration suddenly upon engagement of the suction tip against cortical or lens material, or line clogging.

In these systems, the lines and vent controls are typically presterilized and used only once to avoid the danger of cross-contamination between successive patients. It will be appreciated that if fluid from one patient penetrates a permanent part of the structure, the danger of entry of bacteria back into the flow control device with a new patient remains. Although such devices are usually treated as disposables, this is not a necessary condition.

In an early phase of usage of these systems, a T connector was installed in the flexible lines between the suction tip and the aspiration device. A straight through line provided fluid flow, while the branch arm of the T led through a one-way check valve to a vent device controlled by the foot pedal. This configuration was less than satisfactory, because the T connector was subject to sideways movement that could pinch the lines.

As described in U.S. Pat. No. 4,418,944 in identifying certain prior art, a different "fluid coupling" was known in which a male member having a resilient face could be inserted into a cylindrical receptacle of a female member and subjected to a camming action when rotating into a coupling position. In this position, conduits in the female member and the face of the male member became aligned, so that flow could be established. The patent alleged that no straight-through flow was used with this prior device.

U.S. Pat. No. 4,418,944 therefore proposed that this camming action could be utilized to provide venting in an aspiration-irrigation system, by adding a straight-through fluid connection through the male member. Venting conduits in the face of the male member and in the female receptacle were to be aligned when the male member was engaged in position, and in communication with the straight-through fluid line to provide the desired venting action. This type of male member is now widely used, but has been found to be subject to bacterial intrusion. This occurs both because the irrigation fluid can wet the vent line in the permanent female receptacle and because venting introduces non-sterile air. Although not shown in U.S. Pat. No. 4,418,944, this fluid coupling system also incorporates a pair of check valves in the female receptacle. These valves are subject to accumulation of fluids and salts and further introduce danger of possible clogging and cross-contamination.

Because the aspiration-irrigation equipment is expensive and the male member and flexible tubing are relatively low cost so as to be disposable, and because there is a large inventory in use of the equipmemt itself, it is desirable to be able to employ the existing systems, including the female receptacle. However it is also desirable to provide a male member that will fit into the female receptacle and provide controlled venting action but not be subject to the danger of cross-contamination from air or liquid.

SUMMARY OF THE INVENTION

A superior fluid control coupling in accordance with the invention comprises a male member having a body portion which may be fitted within the female receptacle of an aspiration-irrigation device. The inserted end of the male member has a peripheral wall defining an end recess of substantial cross-sectional area. A hydrophobic membrane spanning an interior portion of this recess lies adjacent to, and in communication with, a straight through aspiration fluid flow path within the male member. The pore size of the membrane is suitable small, such as less than 1.2 microns, to block the passage of bacteria. A resilient gasket filling the end recess provides a deformable end face for engaging the cylindrical recess in the female receptacle. The gasket includes a central bore in the end face that aligns with the vent line in the female receptacle. Within the gasket, this opening diverges substantially in the direction toward the hydrophobic membrane, providing an interior vent opening of substantially large cross-sectional area adjacent the membrane. Advantageously, the body includes an internal peripheral shoulder having a peripheral bead to which the hydrophobic membrane may be securely attached, as by bonding. The flow path for aspiration fluid is straight through the body of the male member, which has fittings at each end to which the flexible tubing may be coupled. A handle extends outwardly from the male member body, so that after inserting in the female receptacle, the male member may be rotated against bearing surfaces adjacent each end to the vent position.

In operating position, air flowing in through the vent line does not permit aspiration fluid to exit the male member, since fluid flow does not penetrate the hydrophobic membrane. The pore size of the membrane provides a barrier to bacteria so that the venting air is sterile. The membrane is above the aspiration line, so there is no restriction on the aspiration flow. The large area of the hydrophobic membrane and the adjacent divergent opening in the gasket mean that there is low pressure drop across the membrane, and relatively free flow of the venting air. Consequently the fluid control device is inserted and operated by a surgeon in a known manner, but assures against contamination from liquid and air sources.

Although the male member may incorporate cam surfaces to be received in the detents in the female receptacle, it may also be rotated into secure venting position against a deformable member that is compressed when the limit position is reached.

BRIEF DESCRIPTION OF THE DRAWINGS

A better understanding of the invention may be had by reference to the following description, taken in conjunction with the accompanying drawings, in which.

DETAILED DESCRIPTION OF THE INVENTION

Figure 1:
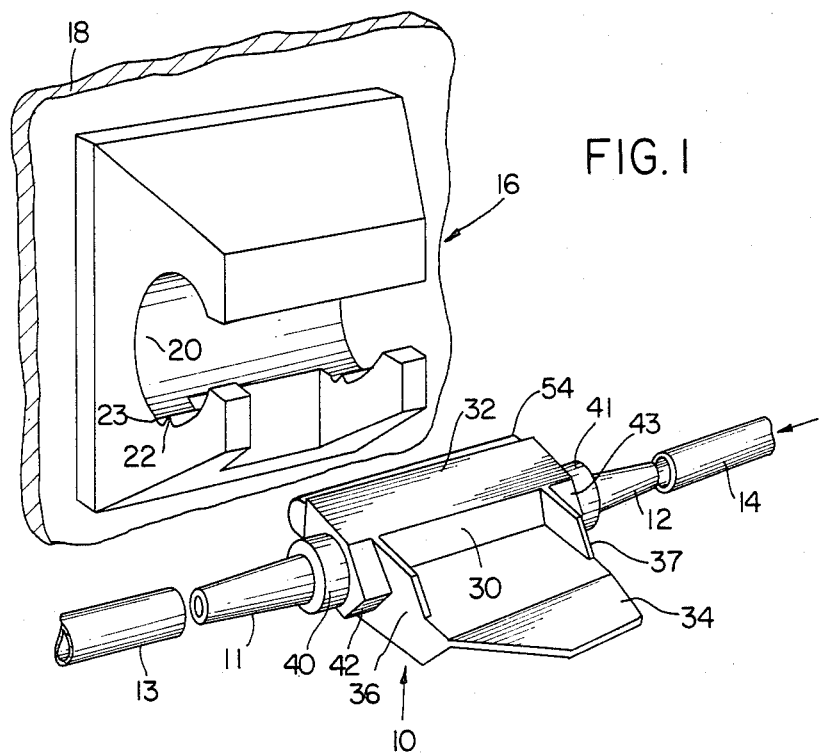
FIG. 1 is a perspective view, partially broken away, of a flow control device in accordance with the invntion as used in conjunction with an existing female receptacle.

Referring now to FIG. 1, a male member 10 in accordance with the invention has a pair of tapering end fittings 11, 12 to which flexible tubing 13, 14 is attached for providing a coupling between a suction tip (not shown) in the region being irrigated, and an aspiration device (not shown) for withdrawing the irrigation fluid and any matter entrained therein. The male member 10 is to be inserted with its free end inside a female receptacle 16 on the known aspiration-irrigation machine (not shown except for the front panel 18). The female receptacle 16 includes a cylindrical recess 20, with an open slot at the front side for receiving the male member 10, as best seen in FIG. 1. The cylindrical recess 20 includes a raised cam 22 and an adjacent detent groove 23 as described in U.S. Pat. No. 4,418,944. An interior vent line 25 within the top of the female receptacle 16 leads downwardly, from the system's control device (not shown) operated via a footswitch by the surgeon, into the wall of the cylindrical recess 20. Inasmuch as this is all a known construction embodied in a widely distributed commerical device, it need not be further described, but reference may be made to U.S. Pat. No. 4,418,944 for further background if desired.

Figure 2:
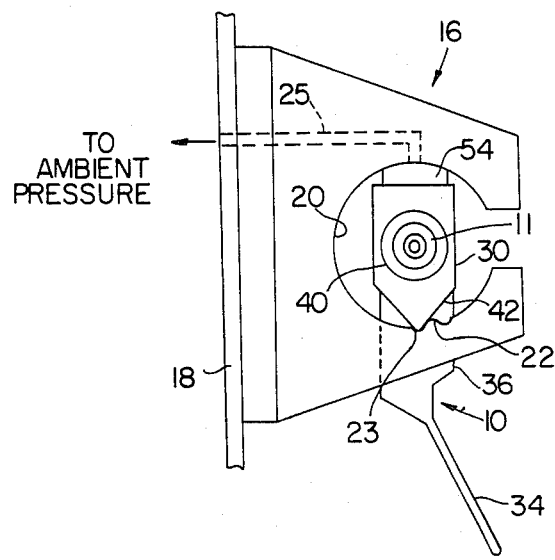
FIG. 2 is a side view of the device of FIG. 1 in the female receptacle.
Figure 6:
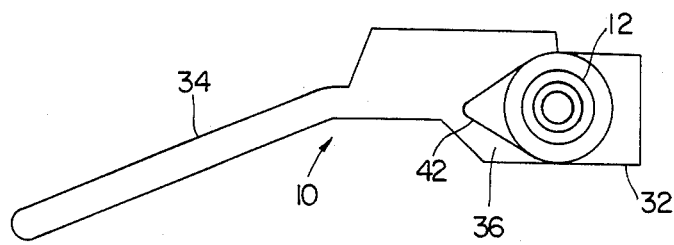
FIG. 6 is a side view of the device of FIGS. 1–4.
Figure 7:
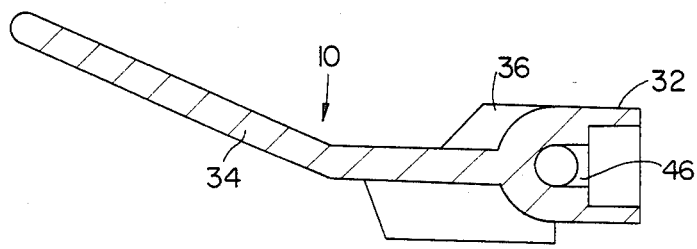
FIG. 7 is a side sectional view of the device of FIGS. 1–6 taken along the lines 7—7 and looking in the direction of the appended arrows.
Figure 3:
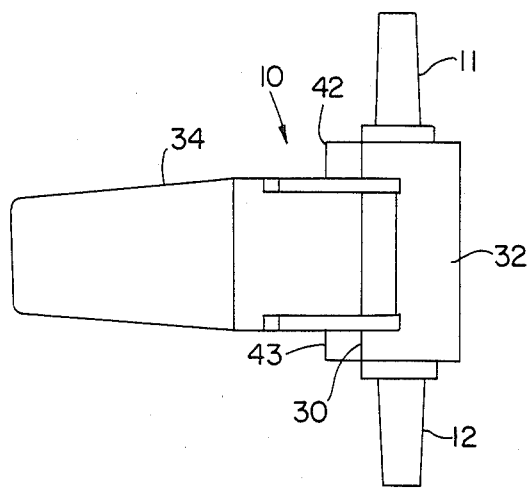
FIG. 3 is a plan view of the device of FIG. 1.
Figure 4:
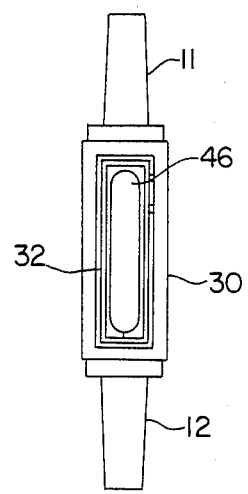
FIG. 4 is an end view of the device of FIGS. 1 and 2.
Figure 8:
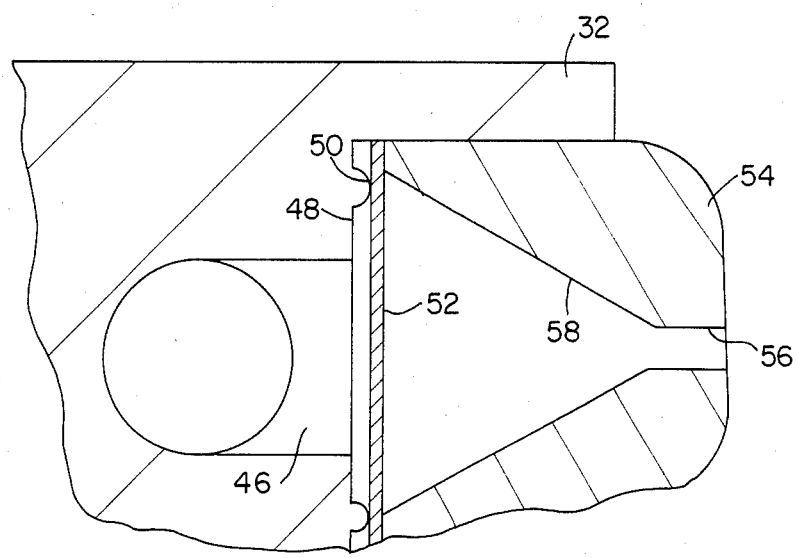
FIG. 8 is an enlarged view of a part of the sectional view of FIG. 7.
Figure 5:
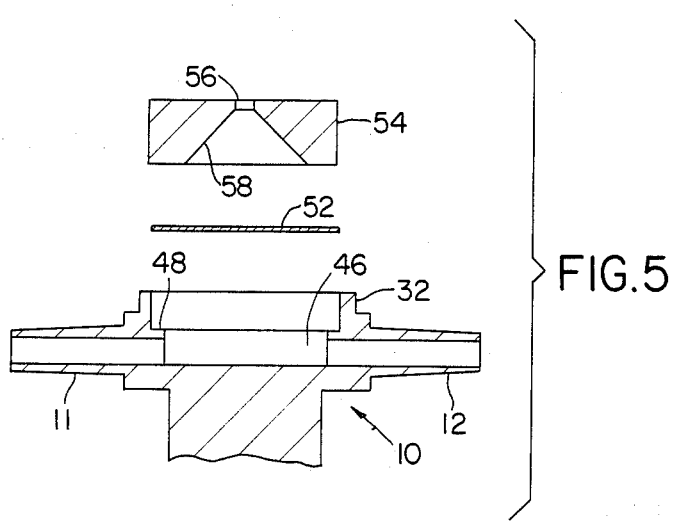
FIG. 5 is an exploded cross-sectional view of the device of FIGS. 1–4.

The male member 10 advantageously comprises three separate parts, the main portion being a molded body 30 including, at the end to be inserted, a peripheral wall 32, here of rectangular outline. The peripheral wall 32 defines an outwardly facing recess spaced apart from the aspiration fluid flow path defined by the center line of the male connector end fittings 11, 12 which are integral with the main body 30. Also integral with the main body 30 is a handle 34 which extends outwardly in the opposite direction from the end recess, the end portion of the handle 34 being angled to be graspable (see FIG. 2) even if the male member 10 is rotated down against the limit position of the female receptacle 16. Referring now to FIGS. 2–4 as well as FIG. 1, the peripheral wall 32 which defines the recess is coupled to the main body 30 and the handle 34 by side bars 36, 37 on each side of the handle 34. Adjacent each end fitting 11, 12 and outside of the peripheral wall 32 the main body 30 includes concentric surfaces 40, 41 about the flow axis that passes through the end fittings 11, 12.

Angled corner elements 42, 43 bear against the surface of the cylindrical recess 20 when the male member 10 is inserted and rotated.

Referring now to FIGS. 4–8 specifically, the peripheral wall 32 defines a substantially rectangular recessed opening in the inserted end of the male member 10, in communication with an interior chamber 46 within the body 30 that is in line with the axial flow path between the end fittings 11, 12. Between the end recess and the interior chamber 46, the recess if narrowed at an offset shoulder 48 which extends around the periphery of the interior chamber 56 and includes a raised bead 50 around its periphery. A hydrophobic membrane 52 is ultrasonically bonded to the offset shoulder 48 at this bead 50, providing a fluid tight hermetic seal. A suitable hydrophobic membrane 52 is supplied by Gelman Sciences Company of Ann Arbor, Mich. under the designation "Versapor". Attached to the interior of the peripheral wall 32 by press fitting within the end recess is a resilient gasket member 54 having a central bore 56 in its protruding end, for alignment with the vent line 25 in the female receptacle 16. The gasket member 54 may alternatively be bonded into place. A diverging opening 58 within the resilient gasket 54 leads from near its outer surface to the hydrophobic membrane 52, and is large enough at this end to be open to the major area of the membrane 52. The gasket 54 protrudes outside the wall 32, and is deformed adequately by the interior cylindrical recess 20 of the female receptacle 16 to seal about the vent line 25 when the male member 10 is in position in the receptacle.

Referring to FIGS. 1 and 2, it can be seen that the male member 10 is insertable into the female receptacle 16 through the open part of the cylindrical recess 20. When fully inserted, the protruding portion of the resilient gasket 54 engages the wall of the cylindrical recess 20. When the handle 34 is rotated downwardly to the limit position the bore 56 is sealed against the continuous surface of the recess 20 and in alignment with the vent line 25. The angled corner elements 42, 43 at each end of the main body 30 and the shape of the gasket 54 on the opposite side retain the male member 10 in position during rotation. Fluid moving axially in the fluid line between the end fittings 11, 12 therefore passes freely through the inner chamber 46 seen best in FIGS. 7 and 8. The hydrophobic membrance 52 forms a side limit or boundary for the aspiration fluid path, but is above the fluid and does not block flow. Further it does not permit egress of the fluid, because the membrane repels water, particle matter and lens fragments.

Venting air drawn in through the bore 56 and the diverging opening 58 is accessible to the entire area of the interior chamber 46, which in this example is about 0.53" long by about 0.20" wide. Consequently, there is only low pressure drop through the hydrophobic membrane 52, even though it forms a barrier to the liquid. The pore size of the hydrophobic membrane 52 is chosed to be in the range of 0.22 to 1.2 microns, being 0.22 microns in this example. At this pore size the membrane 52 constitutes a bacterial barrier as well. Consequently, only sterile air is vented into the system, unlike the prior mechanisms. Since no fluid can enter back up into the vent line to be temporarily or otherwise deposited so as to create a source of possible cross-contamination, the unit can be regarded as a closed sterile system.

The pore size can be varied in accordance with flow rates needed in the system, since the larger the pore size the freer to flow in the vent line. The diverging opening in the gasket can be varied as well in accordance with pore size, since less cross-sectional area is needed as pore size is increased.

Figure 9:
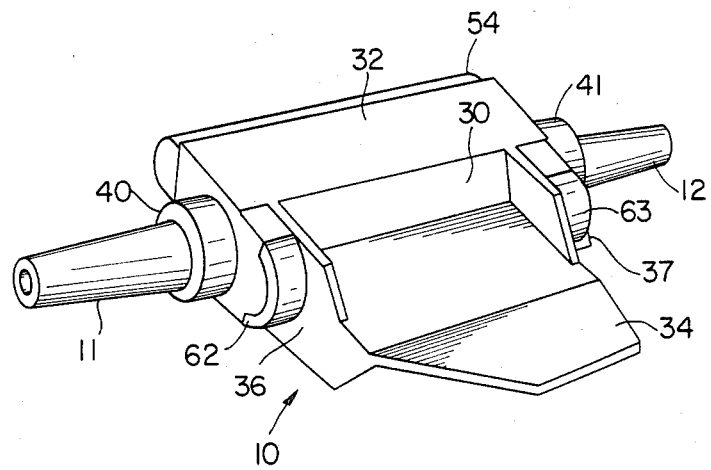
FIG. 9 is a fragmentary perspective view of a portion of an alternative body configuration of a flow control device in accordance with the invention.
Figure 10:
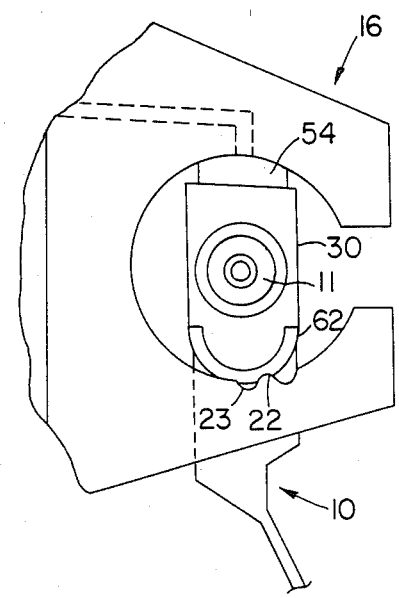
FIG. 10 is a side fragmentary view of the body of FIG. 9 as disposed in a female receptacle in venting position.

The male member 10, shown only in fragmentary form in FIGS. 9 and 10, may have a different external geometry while still rotating within the female receptacle 16 with a positive camming action. As seen in FIGS. 9 and 10, the angled corner elements 42, 43 of FIGS. 1 and 2 are not the only means available for locking the male member 10 into the venting position. A pair of half ring gaskets 62, 63 or rubber, foam or other elastomer are disposed in spaced apart relation on opposite sides along the liquid flow path. Each half ring gasket 62, 63 is also radially opposite the gasket 54, to which it may be secured by adhesive or during molding. Each ring gasket 62, 63 protrudes far enough and is deformable enough to provide firm gripping of the male body member 10 when it is rotated against the limiting surface of the female receptacle 16. Thus the gaskets 62, 63, as seen in FIG. 10, may be deformed to conform at least partially to the contour of the detent groove 23 and ridge 22. Consequently, no detent action or cam surface on the male member 10 are needed to hold the member 10 in the venting position of FIG. 10. The force of the resilient gaskets or retainers may however readily be overcome when the male member 10 is to be rotated so as to be disengaged. Since the male members 10 are typically used only once, wear considerations are not significant although multiple usages are readily feasible.

Although a number of different expedients and modifications have been shown or suggested, it should be appreciated that the invention is not limited thereto but encompasses all forms and variations within the scope of the appended claims.

What is claimed is:

1. A male member for fitting within a female receptacle in an aspiration-irrigation device having an aspiration line, the female receptacle lying along a fluid flow axis for the aspiration line and having a vent line extending therein at a direction substantially normal to the axis, comprising:
   a male member body fitting partially within the female receptacle and having an actuator arm extending therefrom to enable manual rotation of the male member, the body including an open recessed end portion on the intruding side opposite the arm and having an internal chamber lying along the fluid flow axis and connectors for receiving aspiration line tubing at each end thereof, the internal chamber being open to the recessed end portion along substantially its entire length;
   a hydrophobic membrane within the recessed end portion parallel to the fluid flow path within the male member body sealed thereto adjacent the fluid flow axis;
   a resilient gasket disposed and engaged in the recess and protruding therefrom, the gasket having a central orifice therein providing communication between the vent line in the female receptacle and the interior chamber of the male member body via the hydrophobic membrane when the male member body is positioned in vent position.

2. The invention as set forth in claim 1 above, wherein the male member body incudes a peripheral wall defining the open recessed end portion, and wherein the gasket fits within the recessed end portion and protrudes therefrom to provide a seal against the facing surface of the female receptacle.

3. The invention as set forth in claim 2 above, wherein the resilient gasket has a central orifice at its protruding surface and a communicating diverging orifice leading to the hydrophobic membrane.

4. The invention as set forth in claim 3 above, wherein the male member body has bearing surfaces concentric with the fluid flow axis adjacent each side of the open recessed end portion, and an interior peripheral shoulder between the interior chamber and the open recessed end portion, the hydrophobic membrane being ultrasonically bonded to the interior shoulder.

5. The invention as set forth in claim 4 above, wherein the open end recessed portion is rectangular in outline and the interior chamber is approximately 0.125"×0.300" in cross section and wherein the diverging opening in the gasket has a cross-sectional opening at the membrane which is in area a substantial part of the cross-sectional area of the membrane.

6. The invention as set forth in claim 5 above, wherein the interior shoulder includes a raised peripheral bead, the hydrophobic membrane being ultrasonically bonded to the bead, and the resilient gasket being press fit into the open recessed end portion.

7. The invention as set forth in claim 1 above, wherein the male member body includes resilient ring means on surfaces radially opposite the recessed end portion for firmly engaging the male member body to the female receptacle when in vent position.

8. The invention as set forth in claim 1 above, wherein the membrane has a pore size in the range of 0.22 to 1.2 microns.

9. The invention as set forth in claim 8 above, wherein the pore size is about 1.2 microns.

10. A male member for carrying fluid along an axial aspiration path via flexible tubing coupled to each end and removably fittable into a female receptacle having an internal cylindrical wall with a side opening and a side vent line normal to the axial path and intercepting the internal cylindrical wall, the male member being receivable in part within the cylindrical receptacle via the side opening and providing a T coupling to the side vent line to permit flow through the aspiration path and communication between the aspiration path and the side vent line without danger of bacterial contamination or loss of venting action, comprising:
   a unitary body having a pair of spaced apart male end fittings for receiving flexible tubing, the male end fittings being concentrically disposed about the axial aspiration path adjacent an insertion end for the body, the body terminating at the insertion end in a peripheral wall having a substantial cross-sectional area and open to axial aspiration path about a second axis normal thereto, the peripheral wall including an internal shoulder having an interior bead thereon, the unitary body also including a handle extending therefrom in a direction substantially opposite to the insertion end, and external bearing means about the axial flow path for engaging the internal cylindrical wall of the female receptacle when the body is inserted therein via the side opening;
   a hydrophobic membrane sealingly coupled to the interior bead on the internal shoulder of the body to close off the side of the axial aspiration path, the membrane pore size being sufficiently small to block off bacterial flow in the venting stream; and
   a resilient gasket disposed within the peripheral wall and having an aperture therein open to the side vent line when the body is in the vent position, the gasket protuding from the peripheral wall to engaged the internal wall of the female receptacle in sealing relation when in the seal position and including an orifice therethrough aligning with the vent line when the male member is in the vent position, the orifice expanding to encompass a substantial area of the hydrophobic membrane and being press fit into the peripheral wall.

11. The invention as set forth in claim 10 above, wherein the hydrophobic membrane has a pore size less than approximately 1.2 microns.

12. The invention as set forth in claim 11 above, wherein the male member is configured to define an interior chamber at least equal in cross-section to the openings in the end fittings to provide free fluid flow, the interior chamber being open at one side to the cross-sectional area defined by the peripheral wall, and wherein the internal shoulder is adjacent the interior chamber.

* * * * *

UNITED STATES PATENT AND TRADEMARK OFFICE
CERTIFICATE OF CORRECTION

PATENT NO. : 4,722,366

DATED : February 2, 1988

INVENTOR(S) : Armand Maaskamp

It is certified that error appears in the above-identified patent and that said Letters Patent is hereby corrected as shown below:

Column 2, line 24, "suitable" should read --suitably--; line 41, "inserting" should read --insertion--. Column 4, line 10, "if" should read --is--; line 12, "56" should read --46--. Column 5, line 64, "incuds" should read --includes--.

Signed and Sealed this

Third Day of January, 1989

*Attest:*

DONALD J. QUIGG

*Attesting Officer*   *Commissioner of Patents and Trademarks*